(12) United States Patent
Begg

(10) Patent No.: US 11,659,983 B2
(45) Date of Patent: *May 30, 2023

(54) EXPANDING ENDOSCOPE AND METHOD

(71) Applicant: Covidien LP, Mansfield, MA (US)

(72) Inventor: Nikolai Begg, Wellesley, MA (US)

(73) Assignee: Covidien LP, Mansfield, MA (US)

( * ) Notice: Subject to any disclaimer, the term of this patent is extended or adjusted under 35 U.S.C. 154(b) by 259 days.

This patent is subject to a terminal disclaimer.

(21) Appl. No.: 16/936,536

(22) Filed: Jul. 23, 2020

(65) Prior Publication Data

US 2020/0345224 A1 Nov. 5, 2020

Related U.S. Application Data

(63) Continuation of application No. 15/502,570, filed as application No. PCT/US2016/019353 on Feb. 24, 2016, now Pat. No. 10,750,939.

(60) Provisional application No. 62/201,168, filed on Aug. 5, 2015, provisional application No. 62/121,752, filed on Feb. 27, 2015.

(51) Int. Cl.
- *A61B 1/05* (2006.01)
- *A61B 1/00* (2006.01)
- *A61B 1/018* (2006.01)
- *A61B 17/34* (2006.01)
- *A61B 17/32* (2006.01)

(52) U.S. Cl.
CPC ............ *A61B 1/05* (2013.01); *A61B 1/0014* (2013.01); *A61B 1/00098* (2013.01); *A61B 1/00121* (2013.01); *A61B 1/00135* (2013.01); *A61B 1/00183* (2013.01); *A61B 1/018* (2013.01); *A61B 1/053* (2013.01); *A61B 17/320016* (2013.01); *A61B 17/3421* (2013.01)

(58) Field of Classification Search
CPC ............ A61B 1/00121; A61B 1/00135; A61B 1/0014; A61B 1/00183; A61B 1/053
See application file for complete search history.

(56) References Cited

U.S. PATENT DOCUMENTS

| | | |
|---|---|---|
| 5,166,787 A | 11/1992 | Irion |
| 5,351,678 A | 10/1994 | Clayton |
| 5,935,057 A | 8/1999 | Lichtman et al. |
| 6,174,307 B1 | 1/2001 | Daniel et al. |
| 7,591,785 B2 | 9/2009 | Wendlandt et al. |

(Continued)

FOREIGN PATENT DOCUMENTS

| | | |
|---|---|---|
| CN | 103037772 A | 4/2013 |
| WO | 2011085180 A2 | 7/2011 |

OTHER PUBLICATIONS

Examination Report No. 1 issued in corresponding Australian Appl. No. AU 2016222794 dated Jan. 6, 2020 (5 pages).

(Continued)

*Primary Examiner* — Aaron B Fairchild
(74) *Attorney, Agent, or Firm* — Carter, DeLuca & Farrell LLP

(57) ABSTRACT

An endoscope having a camera and a tubular enclosure. A distal end of the camera may be movable from a first position in line with a longitudinal axis of the tubular enclosure to a second position lateral of the longitudinal axis of the tubular enclosure. Some embodiments are configured such that no portion of the endoscope obstructs a view from the distal end of the camera as the distal end of the camera is moved from the first position to the second position.

13 Claims, 10 Drawing Sheets

(56) References Cited

U.S. PATENT DOCUMENTS

| | | |
|---|---|---|
| 7,621,869 B2 | 11/2009 | Ratnakar |
| 10,750,939 B2 | 8/2020 | Begg |
| 2005/0234294 A1 | 10/2005 | Saadat et al. |
| 2005/0272975 A1 | 12/2005 | McWeeney et al. |
| 2007/0213749 A1 | 9/2007 | Kogasaka |
| 2009/0259097 A1 | 10/2009 | Thompson |
| 2009/0318758 A1 | 12/2009 | Farr et al. |
| 2011/0160535 A1 | 6/2011 | Bayer et al. |
| 2012/0245416 A1 | 9/2012 | Viola |
| 2013/0046137 A1 | 2/2013 | Zhao et al. |
| 2014/0180001 A1 | 6/2014 | Grunberg et al. |
| 2014/0228875 A1 | 8/2014 | Saadat |

OTHER PUBLICATIONS

Notification of the First Office Action issued in corresponding Chinese Office Action 201680012034.X dated Dec. 13, 2018 with English translation, 19 pages.

Examination Report issued in corresponding Australian Appl. No. 2016222794 dated Jan. 6, 2020 (5 pages).

European Examination Report issued in corresponding Appl. No. EP 16709872.2 dated Dec. 23, 2020 (5 pages).

Office Action issued in corresponding Canadian Application No. 2,975,885 dated Dec. 23, 2021 (6 pages).

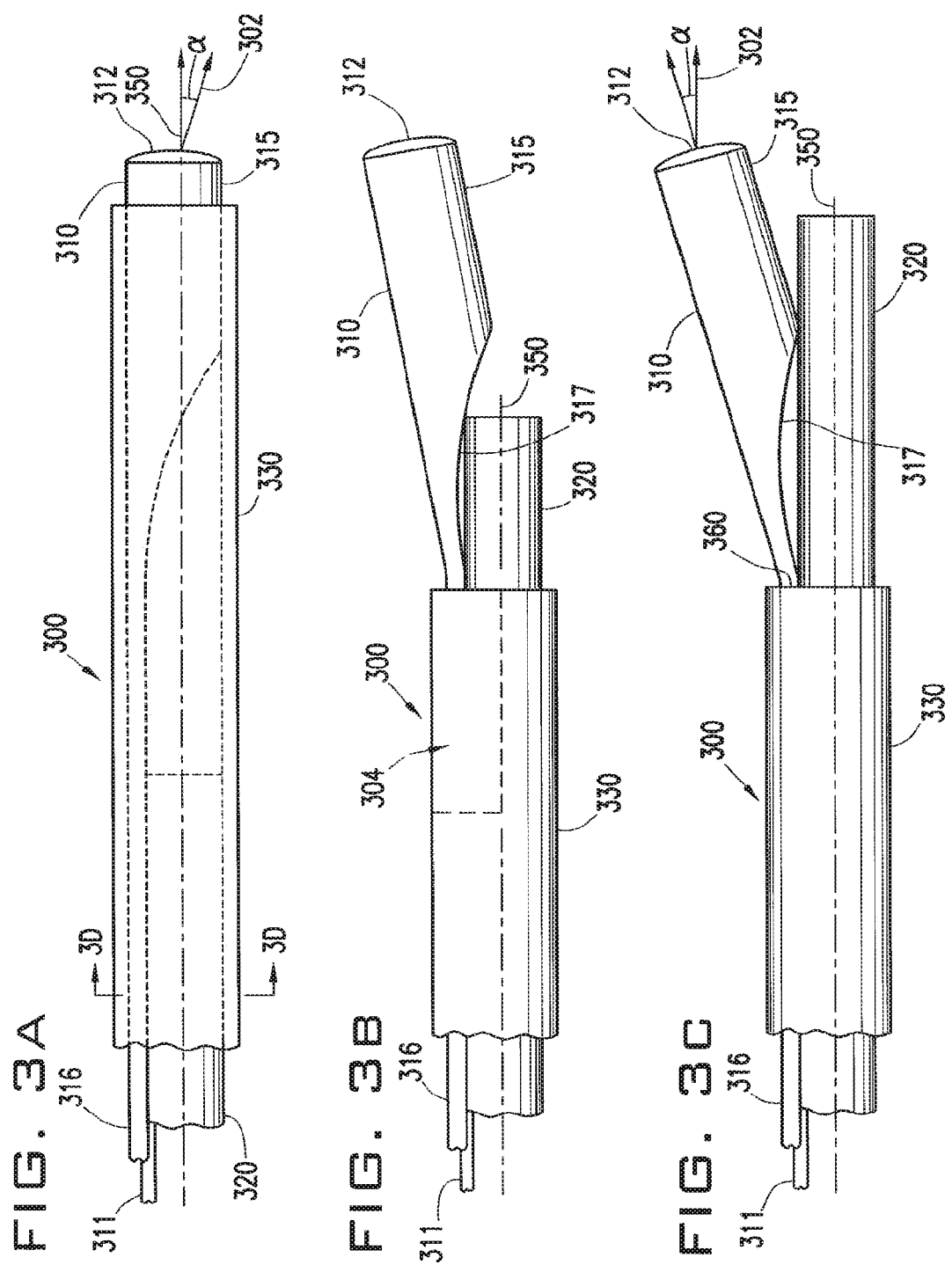

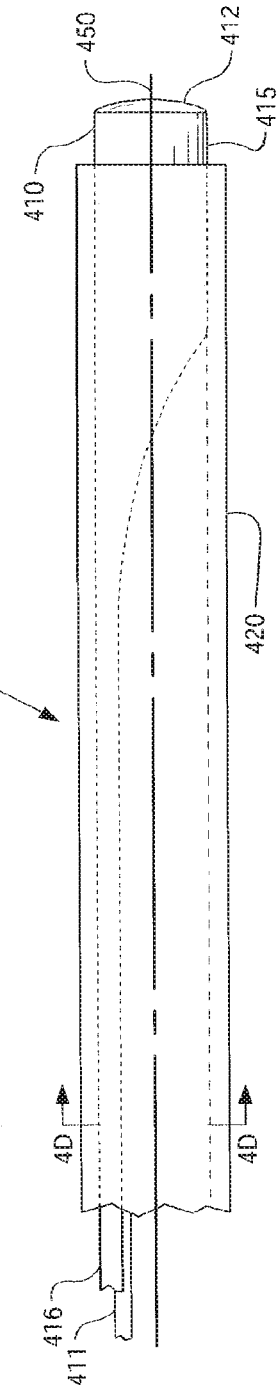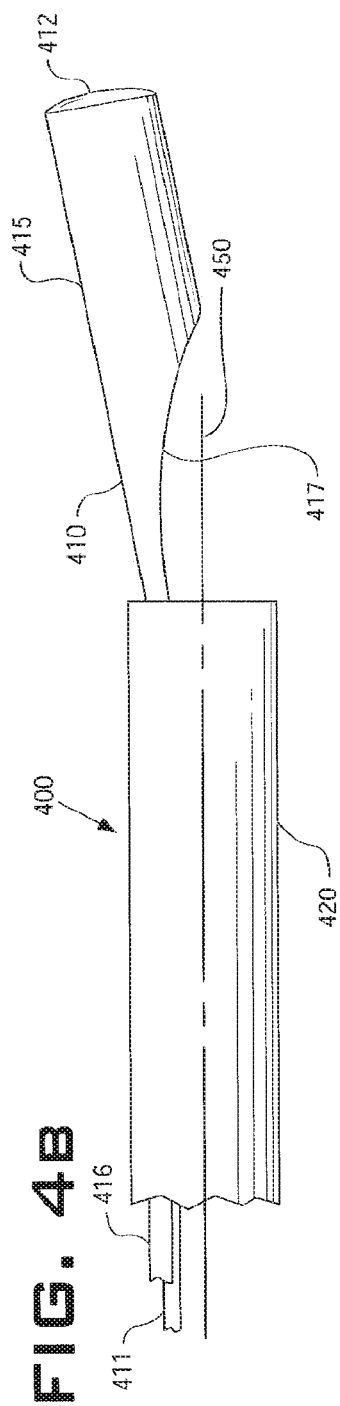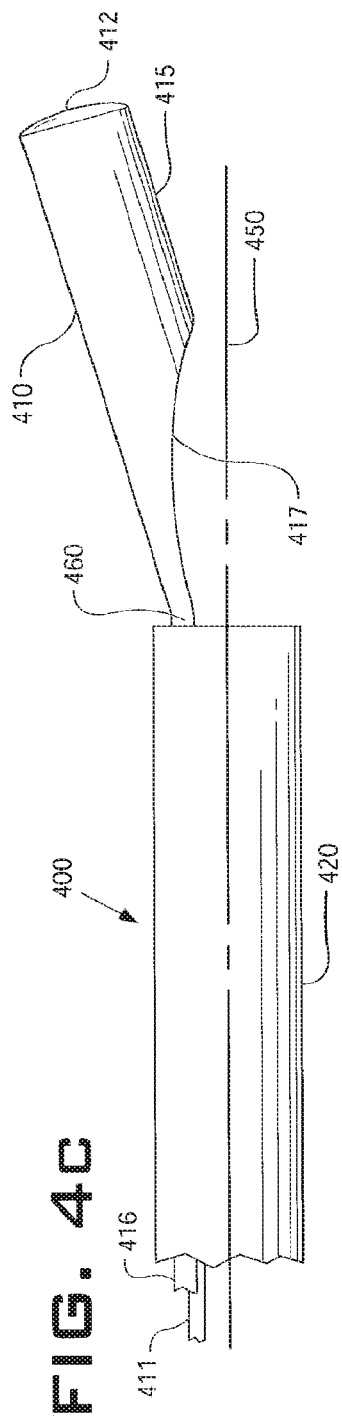

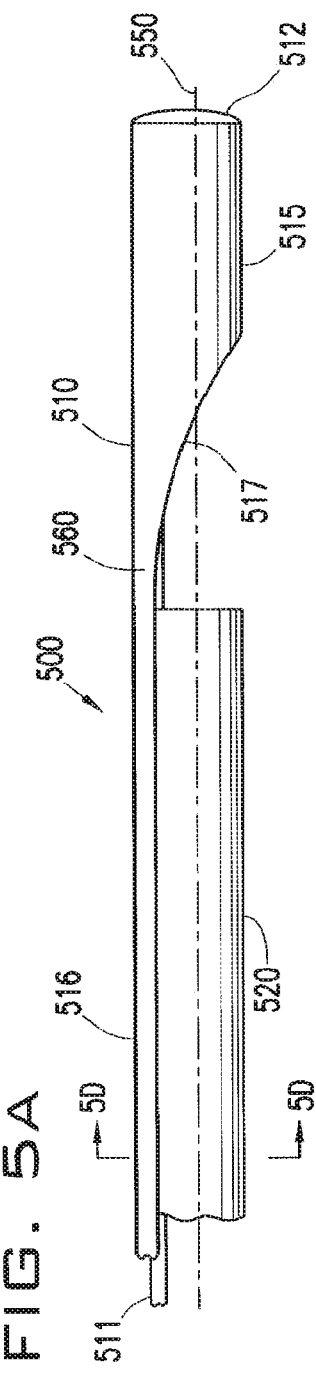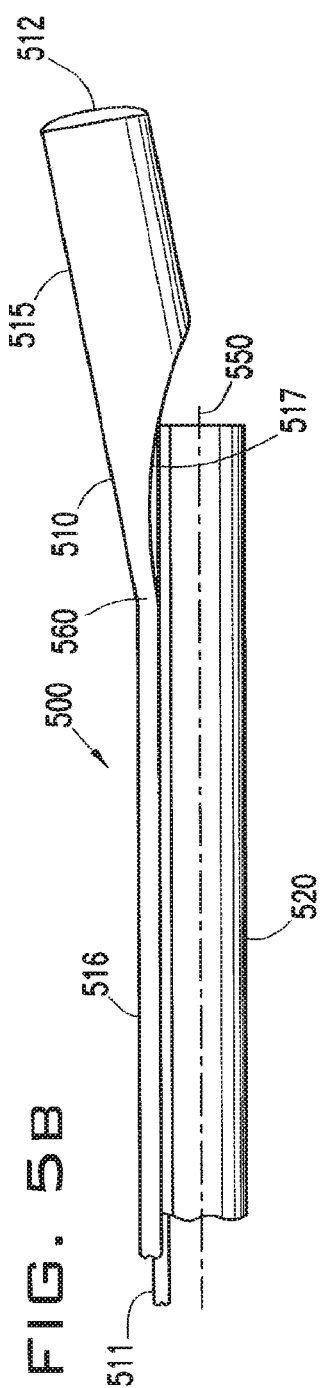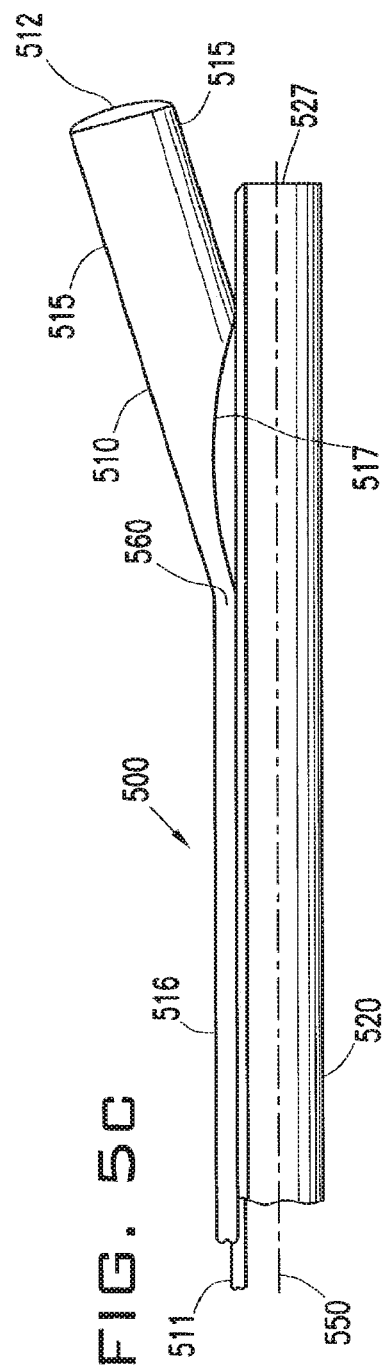

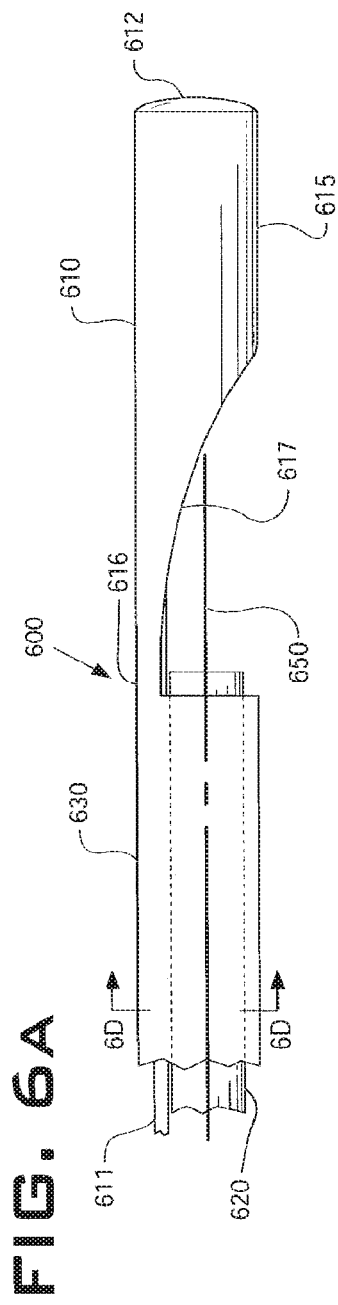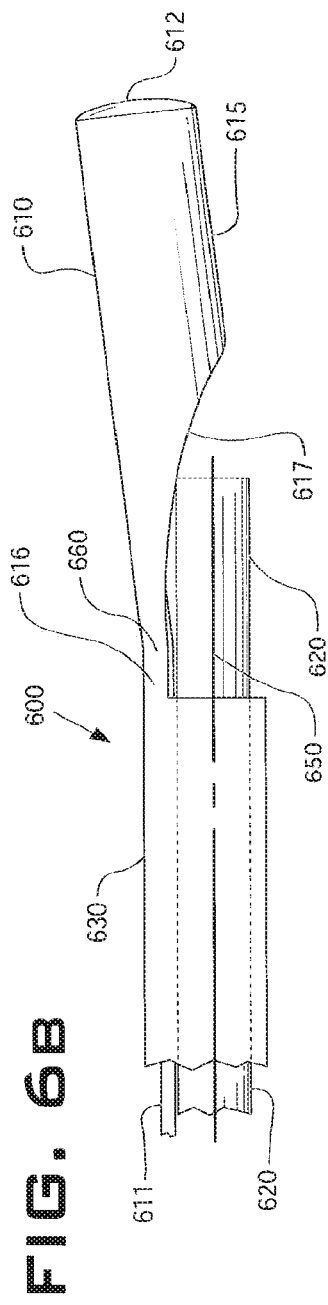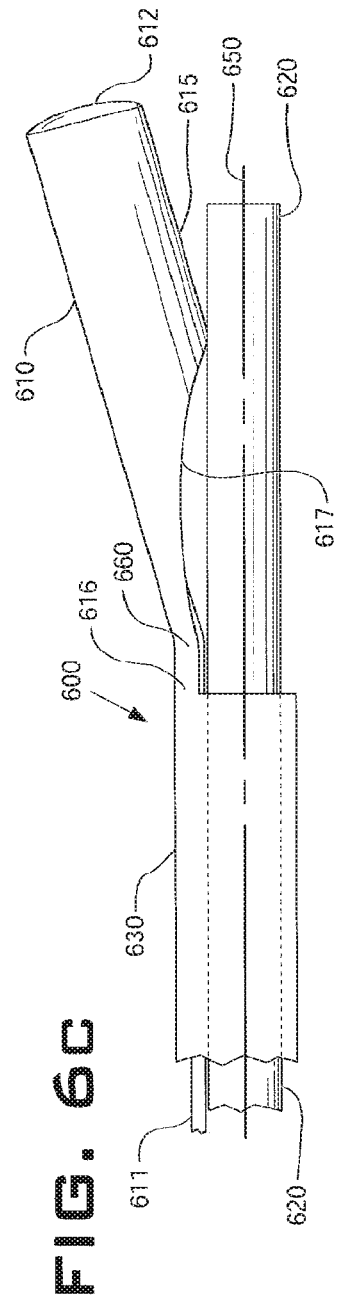

EXPANDING ENDOSCOPE AND METHOD

CROSS-REFERENCE TO RELATED APPLICATIONS

The present application is a continuation application of U.S. patent application Ser. No. 15/502,570, filed Feb. 8, 2017, which is a U.S. National Stage Application under 35 U.S.C. § 371(a) of PCT/US2016/019353 filed Feb. 24, 2016, which claims the benefit of U.S. Provisional App. Ser. No. 62/121,752 filed Feb. 27, 2015, titled "Expanding endoscope with nested components to minimize diameter during insertion," and also claims the benefit of U.S. Provisional App. Ser. No. 62/201,168 filed Aug. 5, 2015, titled "Expanding endoscope and method." All of the above-listed applications are incorporated by reference herein as if reproduced in full below.

FIELD

The present disclosure relates to the field of surgical instruments, and more particularly relates to surgical instruments and methods for endoscopically viewing tissue. Embodiments include laterally shifting a distal end of a camera from a first position to a second position without obstructing a view from the distal end of the camera while shifting between the first and second positions.

BACKGROUND

A "working" section of a medical endoscope may be a distal portion of the endoscope that is inserted into a patient, either through another instrument, or directly into an orifice, incision, or other entry point. In surgical applications, it is often desirable to decrease a working section diameter of instruments to reduce trauma and discomfort to a patient. An endoscope has a diameter that is large enough to contain all of the endoscope's functional components adjacent to one another. These components may include structural and protective members, optical elements, fibers to transfer light for illumination, and channels for instruments or fluid flow. Often a reduction in cross-sectional area of a given component translates into a reduction in functionality or performance of that component. Reducing the size of structural elements may reduce structural integrity and robustness. Smaller optical elements may result in reduced image quality. Fewer or smaller illumination fibres may lead to lower image brightness. Smaller channels may limit instrument compatibility and reduce the rate of fluid flow available to clear debris from an operative field. Consequently, a fundamental trade-off has typically existed in endoscope design between working section diameter and performance. One way to address these inherent limitations is to rigorously assess the functional requirements of the procedure and the needs of the customer to determine the optimal combination of size, functionality, and performance for a given application. Another approach is to develop smaller components that maintain the same or similar functionality and performance. For example, the size of rod lenses has been reduced while maintaining their optical performance. Miniaturized instruments have been developed that engage tissue with the same efficiency as larger devices. Alternative optical technologies, including fibre optic bundles and "chip-on-a-stick" cameras, have been developed that are less fragile and reduce the need for scope structural integrity. Additionally, the relationships between various components may be engineered to decrease overall endoscope size. However, many of these types of advancements present significant cost challenges.

SUMMARY

One embodiment is an endoscope that includes a camera configured to electrically couple to one or more instruments external to the endoscope and a tubular enclosure through which a surgical act may be performed. The tubular enclosure may have a central longitudinal axis, and the camera and the tubular enclosure of some embodiments are movably coupled to one another. In a first coupled position, a distal end of the camera is positioned on the central longitudinal axis of the tubular enclosure, and in a second coupled position the distal end of the camera is located lateral of the central longitudinal axis of the tubular enclosure. Viewing from the camera may be continuously unobstructed by the endoscope at the distal end of the camera while the camera is moved relative to the tubular enclosure from the first coupled position to the second coupled position.

Another embodiment is an endoscope that includes a camera and a tubular enclosure through which a surgical act may be performed. The camera may be coupled to the tubular enclosure in a first position such that a distal end of the camera is positioned along a central longitudinal axis of the tubular enclosure. Embodiments of the endoscope may also include a means for moving the camera from the first position to a second position wherein the distal end of the camera is not positioned on the central longitudinal axis of the tubular enclosure. Viewing from the camera of some embodiments is continuously unobstructed by the endoscope at the distal end of the camera while the camera is moved relative to the tubular enclosure from the first position to the second position.

Still another embodiment is a method of positioning a camera of an endoscope at different perspectives. Method embodiments may include coupling the camera having a distal end to a tubular enclosure having a central longitudinal axis. Method embodiments may also include moving the camera and the tubular enclosure relative to one another to move the distal end of the camera from a first position where the distal end of the camera is positioned on the central longitudinal axis of the tubular enclosure to a second position where the distal end of the camera is not positioned on the central longitudinal axis of the tubular enclosure, without at any time during the movement from the first position to the second position obstructing a view from the distal end of the camera by any portion of the endoscope.

Still another embodiment is a method of resecting tissue. Method embodiments may include inserting, into a surgical site within a patient's body, an endoscope comprising a camera portion and a tubular enclosure associated with the camera, and wherein during the inserting the camera is on a central longitudinal axis of the tubular enclosure. Method embodiments may also include moving the camera lateral of the central longitudinal axis of the tubular enclosure, inserting a resection device through the tubular enclosure, and removing tissue within the surgical site with the resection device while simultaneously viewing the resection by way of the camera.

BRIEF DESCRIPTION OF THE DRAWINGS

FIG. 3A is a side elevation view of the embodiment of the endoscope of FIG. 1 in a first state.

FIG. 3B is a side elevation view of the embodiment of the endoscope of FIG. 1 in a second state.

FIG. 3C is a side elevation view of the embodiment of the endoscope of FIG. 1 in a third state.

FIG. 4A is a side elevation view of an embodiment of an endoscope in a first state.

FIG. 4B is a side elevation view of the embodiment of the endoscope of FIG. 4A in a second state.

FIG. 4C is a side elevation view of the embodiment of the endoscope of FIG. 4A in a third state.

FIG. 5A is a side elevation view of an embodiment of an endoscope in a first state.

FIG. 5B is a side elevation view of the embodiment of the endoscope of FIG. 5A in a second state.

FIG. 5C is a side elevation view of the embodiment of the endoscope of FIG. 5A in a third state.

FIG. 6A is a side elevation view of an embodiment of an endoscope in a first state.

FIG. 6B is a side elevation view of the embodiment of the endoscope of FIG. 6A in a second state.

FIG. 6C is a side elevation view of the embodiment of the endoscope of FIG. 6A in a third state.

DEFINITIONS

Figure 1:
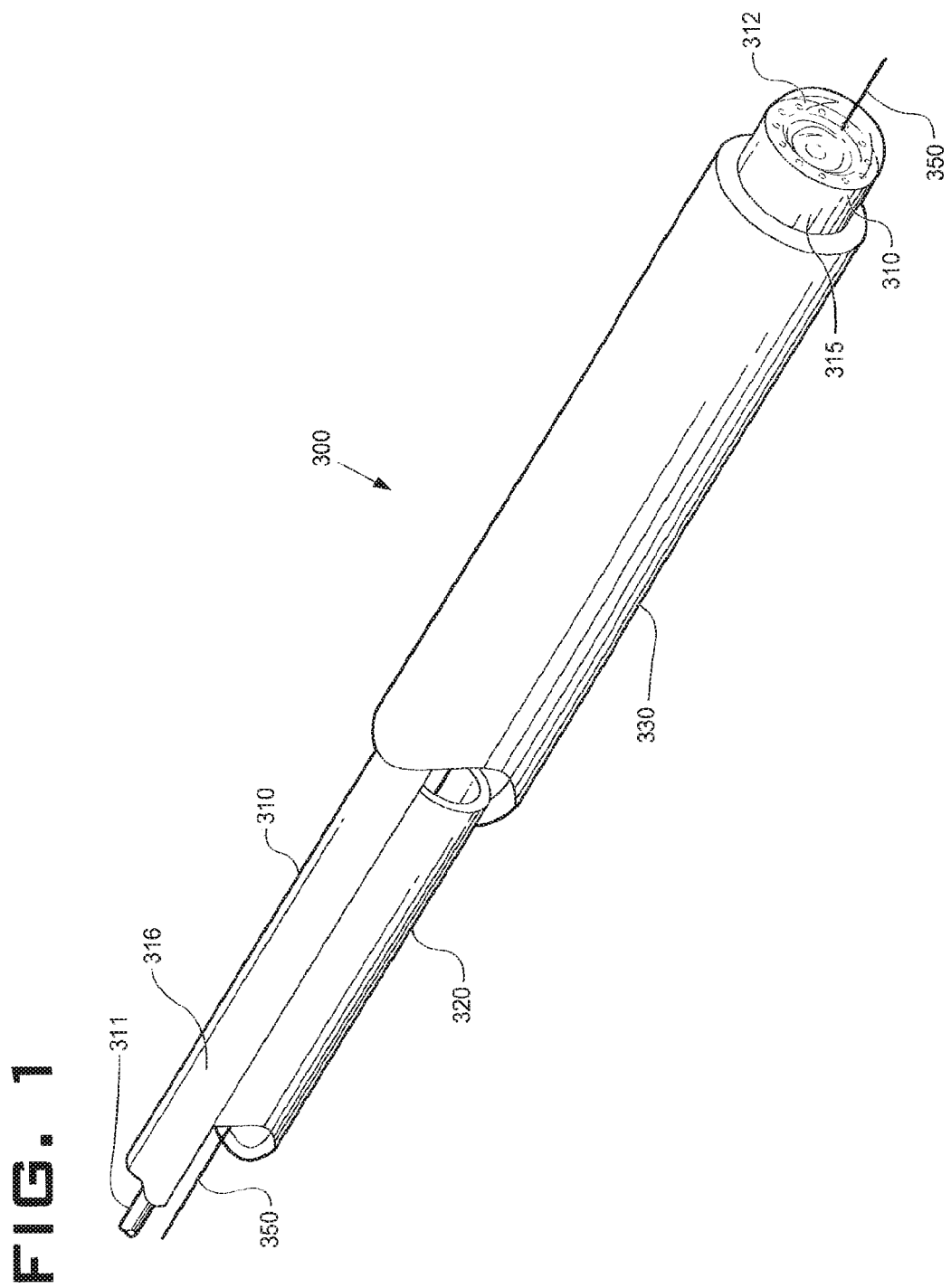
FIG. 1 is a perspective view of an embodiment of an endoscope with partial cut-away of some components.

Certain terms are used throughout the following description and claims to refer to particular system components. As one skilled in the art will appreciate, different companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"Lateral of the central longitudinal axis," in reference to a camera, shall mean that no portion of a distal end of the camera is intersected by the central longitudinal axis.

"On the central longitudinal axis," in reference to a camera, shall mean that at least some portion of a distal end of a camera is intersected by the central longitudinal axis.

"Living hinge" shall mean a hinge defined at a location along a continuous portion of a material, and where the material on either side of the living hinge may be of a different size (measured parallel to an axis of rotation of the hinge) than at the axis of rotation.

DETAILED DESCRIPTION

Embodiments of an endoscope 300, 400, 500, 600, respectively are illustrated in FIGS. 1-6D. Each of the endoscope embodiments 300, 400, 500, 600 includes a camera 310, 410, 510, 610 configured to electrically couple to one or more instruments external to the endoscope 300, 400, 500, 600. The camera 310, 410, 510, 610 may be coupled to any instrument or device that is useful in relaying or displaying information gathered by the camera 310, 410, 510, 610. For example and without limitation, the camera 310, 410, 510, 610 may be electrically coupled to a monitor, recorder, computer, memory device, or any other useful device. The camera 310, 410, 510, 610 may be electrically coupled through a wire, such as wire 311, 411, 511, 611, as illustrated, or may be electrically coupled though a wireless signal by any effective mechanism or of any effective signal type. The illustrated wire 311, 411, 511, 611 is a separate proximally extending member, but in other embodiments may be fully or partially integrated in any proximally extending component of the endoscope 300, 400, 500, 600. The camera 310, 410, 510, 610 of some embodiments may include a field of view that is between 5 degrees and 180 degrees. Some embodiments may more specifically include a field of view substantially between 80 degrees and 90 degrees.

The "field of view" refers to the angle of capture of images (e.g., a picture taken with a fish-eye lens has a wide field of view, while a picture taken with a telephoto lens has a narrow field of view). A related concept is direction of view, where direction of view is a line extending along the center of the field of view. Direction of view can be measured against any suitable reference, such as a longitudinal axis of a component, with the angle between the reference and the direction of view referred to as the "field angle." With these definitions in mind, the camera 310, 410, 510, 610 of some embodiments may include a direction of view that resides along a longitudinal axis of the camera 310, 410, 510, 610 (i.e., a zero degree field angle relative to the longitudinal axis of the camera). In other embodiments, the direction of view may be skewed from the longitudinal axis of the camera 310, 410, 510, 610 (i.e., a non-zero field angle relative to the longitudinal axis of the camera). A camera with a skewed direction of view may be useful in providing a broader view during insertion. Example insertion configurations are illustrated in FIGS. 3A, 4A, 5A, and 6A. With a skewed direction of view, rotation of the endoscope 300, 400, 500, 600 would enable a user to survey a wider area around the end of the endoscope. In other cases, the camera 310, 410, 510, 610 direction of view may be coordinated with the potential displacement of the camera 310, 410, 510, 610, as shown respectively in FIGS. 3B, 3C, 4B, 4C, 5B, 5C, 6B, 6C, such that when fully or partially displaced, the direction of view is parallel to the central longitudinal axis 350, 450, 550, 650 of a tubular enclosure 320, 420, 520, 620. One or both of a light and fibre optic light strands may be integrated into any component of or added to the endoscope 300, 400, 500, 600, as may be useful in providing light for viewing through the camera 310, 410, 510, 610.

Embodiments of an endoscope 300, 400, 500, 600 include the tubular enclosure 320, 420, 520, 620 through which a surgical act may be performed. The camera 310, 410, 510, 610 and the tubular enclosure 320, 420, 520, 620 are movably coupled to one another. In a first coupled position, as shown respectively in FIGS. 3A, 4A, 5A, 6A, the distal end 312, 412, 512, 612 of the camera 310, 410, 510, 610 is positioned on the central longitudinal axis 350, 450, 550, 650 of the tubular enclosure 320, 420, 520, 620. In a second coupled position, as shown respectively in FIGS. 3B and 3C, 4B and 4C, 5B and 5C, 6B and 6C, the distal end 312, 412, 512, 612 of the camera 310, 410, 510, 610 is located lateral of the central longitudinal axis 350, 450, 550, 650 of the tubular enclosure 320, 420, 520, 620. As used herein, the term "lateral of the central longitudinal axis" means that no portion of a distal end of a camera is intersected by the central longitudinal axis. The term "on the central longitudinal axis" means that at least some portion of a distal end of a camera is intersected by the central longitudinal axis. The distal end of a camera may include not only the very far distal tip of a camera but also portions of the camera near the very far distal tip. In the embodiments illustrated, viewing from the camera 310, 410, 510, 610 is continuously unobstructed by the endoscope 300, 400, 500, 600 at the distal end 312, 412, 512, 612 of the camera 310, 410, 510, 610 while the camera 310, 410, 510, 610 is moved relative to the tubular enclosure 320, 420, 520, 620 from the first coupled position to the second coupled position. Stated another way, in some embodiments, no portion of the endoscope 300, 400, 500, 600 is positioned distally of the distal end 312, 412, 512, 612 of the camera 310, 410, 510, 610 while the camera 310, 410, 510, 610 is moved relative to the tubular enclosure 320, 420, 520, 620 from the first coupled position to the second coupled position. Stated yet another way, in some embodiments, unobstructed viewing is a result of a structure where the distal end 312, 412, 512, 612 of the camera 310, 410, 510, 610 is the most distal element of the endoscope 300, 400, 500, 600. More specifically, the distal end 312, 412, 512, 612 of the camera 310, 410, 510, 610 may be the most distal element of the endoscope 300, 400, 500, 600 during movement from the first coupled position to the second coupled position.

As illustrated in FIGS. 1-3E, the endoscope 300 also includes a sheath 330 in which the camera 310 and the tubular enclosure 320 are sized to fit. The tubular enclosure 320 shown is a cannula capable of longitudinally sliding relative to the sheath 330 and relative to the camera 310. The tubular enclosure 320 is open at both its proximal and distal ends and includes solid walls. However, in other embodiments proximal and distal ends may be partially closed or closable and the walls may not extend completely around the perimeter of the tubular enclosure at some or all longitudinal distances along the tubular enclosure. Some embodiments of a tubular enclosure may include a distal end that is rounded or chamfered to lessen stresses at points of contact with other components that are distal of the tubular enclosure when the endoscope is change between states. To the extent that reference is made to a central longitudinal axis 350 extending from a tubular enclosure that is curved along all or part of its length, the central longitudinal axis 350 may be considered to extend substantially normally from a distal end of the tubular enclosure.

The camera 310 comprises camera body 315 that defines a distal end 312 of the camera 310. In example embodiments the camera body 315 proximate to the distal end 312 has a circular cross section, and thus a circumferential length that fully encircles the central longitudinal axis 350 (when the camera 310 is in the configuration shown in FIG. 3A). The proximally extending member 316 in the example embodiments is contiguous with the camera body 315, and in the example shown the circumferential length of the proximally extending member 316 does not fully encircle the central longitudinal axis 350 (as best shown in the cross-sectional view of FIG. 3D). Measured as angle about (and perpendicular to) the central longitudinal axis 350, the proximally extending member 316 spans a non-zero value less than 180 radial degrees, in some cases a non-zero value less than 90 radial degrees, and in other cases the proximally extending member 316 spans about 70 radial degrees.

Figure 2:
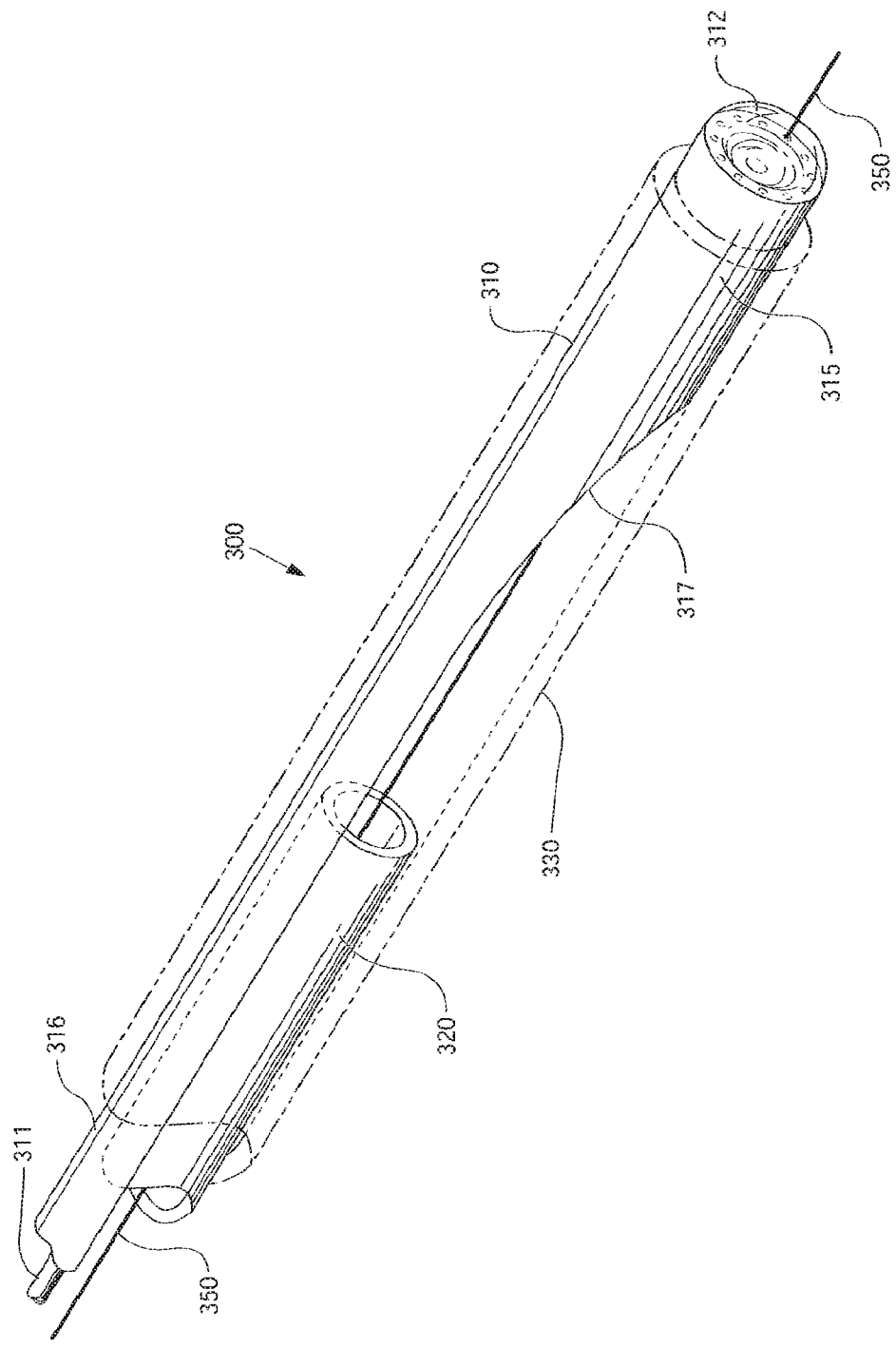
FIG. 2 is a perspective view of the embodiment of the endoscope of FIG. 1 with partial cut-away of some components and with limited visibility of some components.

The camera 310 depicted is also capable of longitudinally sliding relative to the sheath 330. For example, the endoscope 300 may be introduced into tissue with the camera 310 fully or substantially retracted within the sheath 330, as shown in FIG. 3A. In FIGS. 3B and 3C, the camera 310 is shown following longitudinal sliding relative to the sheath 330 to enable the camera 310 to be in a position to be further acted on by the tubular enclosure 320. The camera 310 shown includes the camera body 315 with the distal end 312 and a proximally extending member 316 that is coupled to the camera body 315. In some embodiments, one or both of the proximally extending member 316 and the camera body 315 may include along at least part of their lengths a lateral spring force configured to bias one or both of the proximally extending member 316 and the camera body 315 into a curved shape. For example, lateral spring forces may exist in the components that tend to push the distal end 312 away from the central longitudinal axis 350 of the tubular enclosure 320. In the alternative, lateral spring forces may exist in the components that tend to push the distal end 312 toward the central longitudinal axis 350 of the tubular enclosure 320 so that, in the example shown in the second and third states of FIGS. 3B and 3C a resistive force is maintained by the camera 310 against the tubular enclosure 320 as the tubular enclosure 320 is advanced distally. Lateral spring forces of some embodiments may exist along the entire lengths of the proximally extending member 316 and the camera body 315 or may be limited to specific segments of either. As shown in FIGS. 2, 3B, and 3C, the camera 310 may include a proximally directed surface 317 shaped so that when the proximally directed surface 317 is contacted by the tubular enclosure 320, the tubular enclosure 320 moves the camera 310 from the first coupled position toward the second coupled position. As shown in the example system, the proximally directed surface 317 is a curved surface. The radius of curvature R (FIG. 3E) may be at least twice the outside diameter (OD) of the camera body 315, in some cases at least four times the OD of the camera body 315, and in a specific case the radius of curvature is 5 times the OD of the camera body.

In some embodiments, the proximally directed surface may include compound curved surfaces that interact with a tubular enclosure to control rates and amounts of deflections of the camera 310 in response to movements of the tubular enclosure 320. In some embodiments, a proximally directed surface may have one or more planar surfaces with at least one surface being in a different plane from surfaces of the tubular enclosure 320 configured to contact the proximally directed surface.

The movable coupling between the camera 310 and the tubular enclosure 320 includes a mechanism for longitudinal sliding between the camera 310 and the tubular enclosure 320, as illustrated in the changes of relative state illustrated in FIGS. 3A-3C. In addition, in the illustrated embodiment, the movable coupling between the camera 310 and the tubular enclosure 320 includes a mechanism for movement substantially about an axis 360 (FIG. 3C) perpendicular to the central longitudinal axis 350 of the tubular enclosure 320. The illustrated embodiment shows a living hinge between the camera 310 and the tubular enclosure 320 to the extent that the living hinge at the axis 360 is within a portion of the camera 310 between the camera body 315 and the proximally extending member 316, and the proximally extending member 316 is not rotationally movable relative to the tubular enclosure 320. In other embodiments, the illustrated living hinge may be replaced or supplemented by one or more pinned hinges.

Figure 3D:
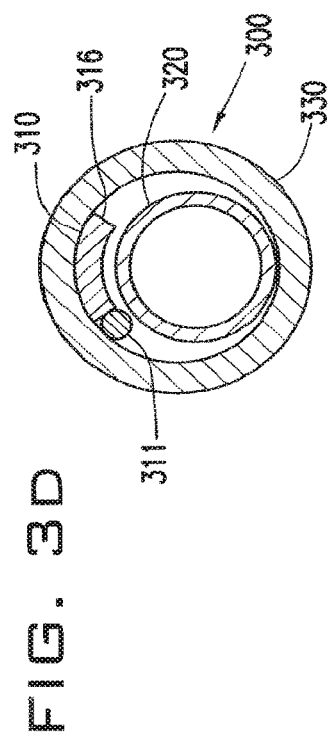
FIG. 3D is a cross-sectional view of the embodiment of the endoscope of FIG. 3A.
Figure 3E:
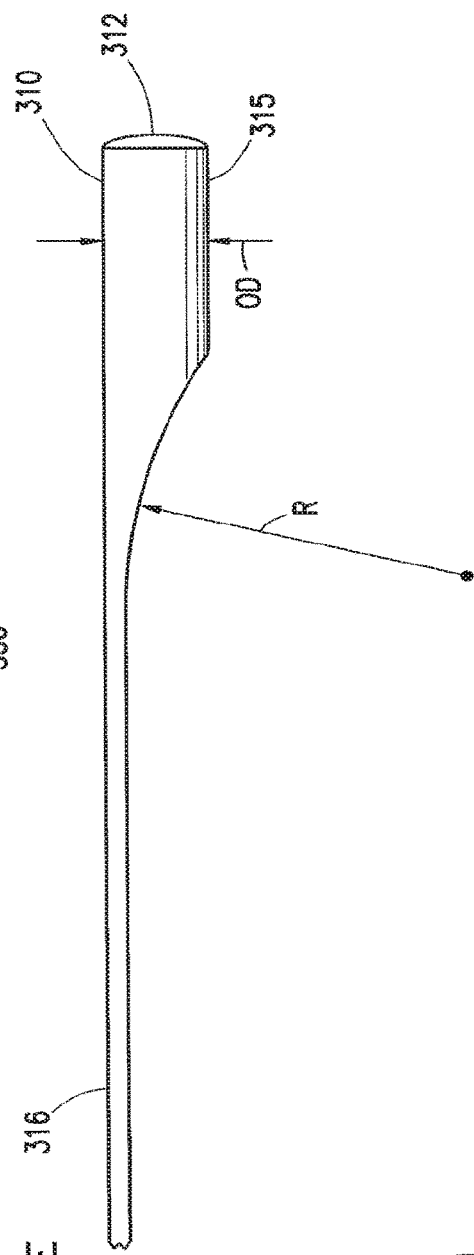
FIG. 3E is a side elevation view of an embodiment of a camera in accordance with an example embodiment.

FIGS. 3A and 3D also show an example direction of view. In particular, FIG. 3A shows the example camera has a longitudinal axis that is coaxial with the central longitudinal axis 350, and the direction of view 302 is skewed from the central longitudinal axis 350 thus forming a field angle α. Thus, during insertion of the endoscope 300 in the configuration of FIG. 3A, the direction of view 302 is not parallel to the central longitudinal axis 350. However, the field angle α is selected such that when the camera 310 is fully extended and in the second coupled position (FIG. 3C), the direction of view 302 is substantially parallel to the central longitudinal axis 350 (and the field angle α is measured with respect to the longitudinal axis 303 of the camera 315. The field angle α, and thus the direction of view 302, may be implemented by a prism (not specifically shown) associated with the camera 310. The same field angles and directions of view may be implemented in any of the embodiments discussed herein.

Referring to FIG. 3B, in some example embodiments the sheath 330 may include a window or cut-out 304 (shown in dashed lines) to enable the camera 310 to move transversely (e.g., to the orientation shown in FIG. 3C) without requiring as much relative movement of the sheath 330 on the one hand, and the camera 310 and tubular enclosure 320 on the other hand.

Figure 4:
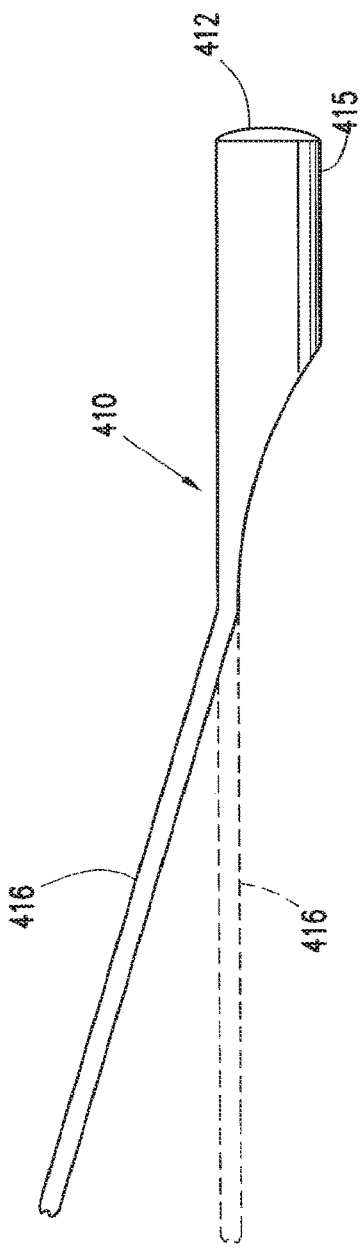
FIG. 4 is a side elevation view of an embodiment of a camera representing a flexed state and a lateral spring tensioned state.
Figure 4D:
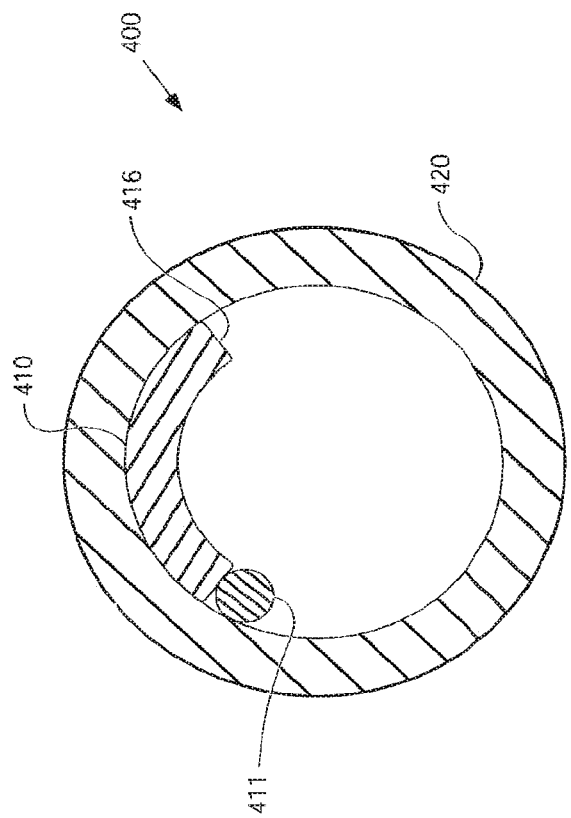
FIG. 4D is a cross-sectional view of the embodiment of the endoscope of FIG. 4A.

As illustrated in FIGS. 4-4D, the tubular enclosure 420 of endoscope 400 is a sheath in which the camera 410 is sized to fit. The camera 410 shown is capable of longitudinally sliding relative to the tubular enclosure 420. The tubular enclosure 420 is open at both its proximal and distal ends and includes solid walls. However, in other embodiments proximal and distal ends may be partially closed or closable and the walls may not extend completely around the perimeter of the tubular enclosure at some or all longitudinal distances along the tubular enclosure. Some embodiments of a tubular enclosure may include a distal end that is rounded or chamfered. To the extent that reference is made to a central longitudinal axis 450 extending from a tubular enclosure that is curved along all or part of its length, the central longitudinal axis 450 may be considered to extend substantially normally from a distal end of the tubular enclosure.

The camera 410 shown includes a camera body 415 with the distal end 412 and a proximally extending member 416 that is coupled to the camera body 415. In some embodiments, one or both of the proximally extending member 416 and the camera body 415 may include along at least part of their lengths a lateral spring force configured to bias one or both of the proximally extending member 416 and the camera body 415 into a curved shape. The proximally extending member 416 is shown in FIG. 4 with a lateral spring force. The dashed lines show the proximally extending member 416 aligning with the longitudinal axis of the camera body and represent a configuration where the proximally extending member 416 would be under a lateral spring force. The solid lines for the proximally extending member 416 represent a state where the lateral spring force is released. In the embodiment depicted, the lateral spring forces induced by inserting the camera 410 into the tubular enclosure 420 tend to push the distal end 412 away from the central longitudinal axis 450 of the tubular enclosure 420, as illustrated in FIGS. 4B and 4C. Lateral spring forces may be designed into the entire lengths of the proximally extending member 416 and the camera body 415 or may be limited to specific segments of either. The endoscope 400 may be introduced into tissue with the camera 410 fully or substantially retracted within the tubular enclosure 420, as shown in FIG. 4A. In FIGS. 4B and 4C, the camera 410 is shown following longitudinal sliding relative to the tubular enclosure 420. As the camera 410 is moved beyond a distal end of the tubular enclosure 420, the lateral spring forces in the proximally extending member 416 are released and push the distal end 412 away from the central longitudinal axis 450 of the tubular enclosure 420. This movement results in the distal end 412 of the camera 410 being moved from the first coupled position, represented in FIG. 4A, to the second coupled position, represented in both of FIGS. 4B and 4C.

The endoscope 400 illustrated does not require an additional component to be pressed against the camera 410 to move the distal end 412 of the camera 410 away from the central longitudinal axis 450 due to the orientation and degree of later spring force induced in the components of the camera 410. However, an additional cannula may be used with the endoscope 400 to provide a smoother working channel or to positively move portions of the camera 410 out of a working area within the tubular enclosure 420. In a situation where an additional cannula were to be used, the camera 410 may include a proximally directed surface 417 shaped so that when the proximally directed surface 417 is contacted by the additional cannula similarly to the interactions of the tubular enclosure 320 and the proximally directed surface 317 noted above.

The movable coupling between the camera 410 and the tubular enclosure 420 includes a mechanism for longitudinal sliding between the camera 410 and the tubular enclosure 420, as illustrated in the changes of relative state illustrated in FIGS. 4A-4C. In addition, in the illustrated embodiment, the movable coupling between the camera 410 and the tubular enclosure 420 includes a mechanism for movement substantially about an axis 460 (FIG. 4C) perpendicularly to the central longitudinal axis 450 of the tubular enclosure 420. The illustrated embodiment shows a living hinge between the camera 410 and the tubular enclosure 420 to the extent that the living hinge at the axis 460 is within a portion of the camera 410 between the camera body 415 and the proximally extending member 416, and the proximally extending member 416 is not rotationally movable relative to the tubular enclosure 420. In other embodiments, the illustrated living hinge may be replaced or supplemented by one or more pinned hinges. The relative circumferential lengths of the proximally extending member 416 and the camera body 415 may be as described above in reference to the proximally extending member 316 and the camera body 315. FIG. 4D shows the proximally extending member 416 within the tubular enclosure 420, along with the wire 411.

Figure 5D:
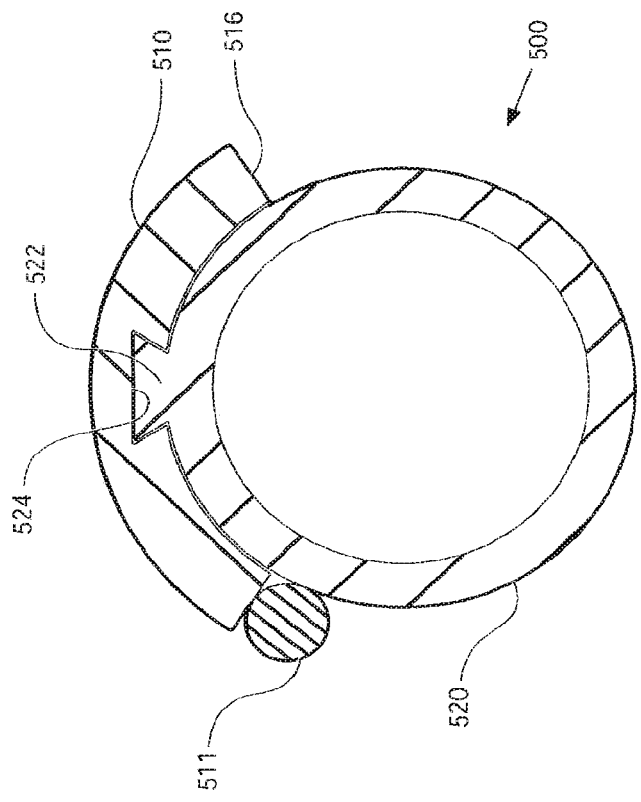
FIG. 5D is a cross-sectional view of the embodiment of the endoscope of FIG. 5A.
Figure 6D:
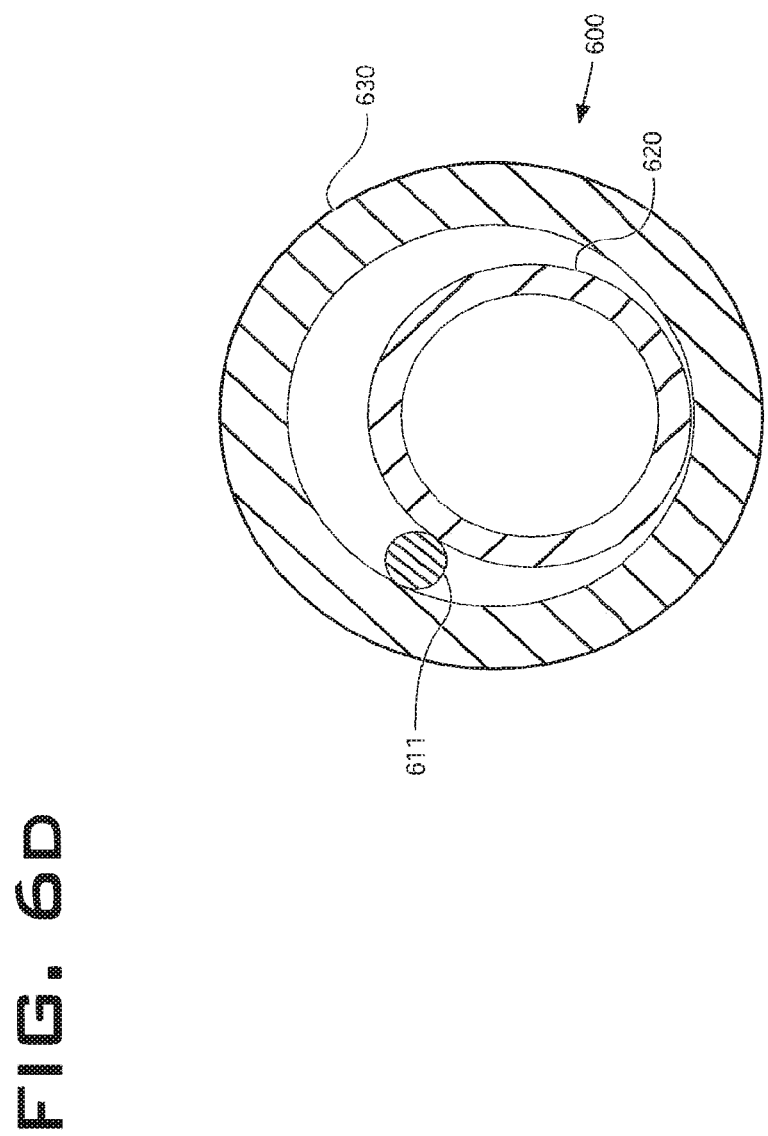
FIG. 6D is a cross-sectional view of the embodiment of the endoscope of FIG. 6A.

As illustrated in FIGS. 5-5D, the tubular enclosure 520 is a cannula capable of longitudinally sliding relative to the camera 510. In the embodiment shown, the tubular enclosure 520 and the camera 510 are movably coupled to one another such that the tubular enclosure 520 and the camera 510 will not move laterally away from one another at locations where the tubular enclosure 520 and the camera are coupled. In particular, in this embodiment, the tubular enclosure 520 includes a dovetail spline 522 and the camera 510 includes a dovetail notch 524 (FIG. 5D). The longitudinal axis of the dovetail joint formed between the dovetail spline 522 and the dovetail notch 524 is substantially parallel with the central longitudinal axis 550 of the tubular enclosure 520. In some embodiments having a dovetail joint, a dovetail spline may be on a camera and a dovetail notch may be on a tubular enclosure. Other similar embodiments may achieve a longitudinally sliding but non-moving lateral coupling by any effective mechanism, including mechanisms that do not use of a dovetail joint.

The tubular enclosure 520 depicted is open at both its proximal and distal ends and includes solid walls. However, in other embodiments proximal and distal ends may be partially closed or closable and the walls may not extend completely around the perimeter of the tubular enclosure at some or all longitudinal distances along the tubular enclosure. Some embodiments of a tubular enclosure may include a rounded distal surface or a chamfered distal surface 527 (FIG. 5C) to lessen stresses at points of contact with other components that are distal of the tubular enclosure when the endoscope is change between states. To the extent that reference is made to a central longitudinal axis 550 extending from a tubular enclosure that is curved along all or part of its length, the central longitudinal axis 550 may be considered to extend substantially normally from a distal end of the tubular enclosure.

The camera 510 shown includes a camera body 515 with the distal end 512 and a proximally extending member 516 that is coupled to the camera body 515. In some embodiments, one or both of the proximally extending member 516 and the camera body 515 may include along at least part of their lengths a lateral spring force configured to bias one or both of the proximally extending member 516 and the camera body 515 into a curved shape. For example, lateral spring forces may exist in the components that tend to push the distal end 512 away from the central longitudinal axis 550 of the tubular enclosure 520. In the alternative, lateral spring forces may exist in the components that tend to push the distal end 512 toward the central longitudinal axis 550 of the tubular enclosure 520. Lateral spring forces of some embodiments may exist along the entire lengths of the proximally extending member 516 and the camera body 515 or may be limited to specific segments of either. As shown in FIGS. 5A-5C, the camera 510 may include a proximally directed surface 517 shaped so that when the proximally directed surface 517 is contacted by the tubular enclosure 520, the tubular enclosure 520 moves the camera 510 from the first coupled position toward the second coupled position. As shown in this example, the proximally directed surface 517 is a curved surface, and the radius of curvature may be as described in reference to FIG. 3E above. In some embodiments, a proximally directed surface may include compound curved surfaces that interact with a tubular enclosure to control rates and amounts of deflections of the camera 510 in response to movements of the tubular enclosure 520. In some embodiments, a proximally directed surface may have one or more planar surfaces with at least one surface being in a different plane from surfaces of the tubular enclosure 520 configured to contact the proximally directed surface.

The movable coupling between the camera 510 and the tubular enclosure 520 includes a mechanism for longitudinal sliding between the camera 510 and the tubular enclosure 520, as illustrated in the changes of relative state illustrated in FIGS. 5A-5C. In addition, in the illustrated embodiment, the movable coupling between the camera 510 and the tubular enclosure 520 includes a mechanism for movement substantially about an axis 560 (FIGS. 5A-5C) perpendicular to the central longitudinal axis 550 of the tubular enclosure 520. The illustrated embodiment shows a living hinge between the camera 510 and the tubular enclosure 520 to the extent that the living hinge at the axis 560 is within a portion of the camera 510 between the camera body 515 and the proximally extending member 516, and the proximally extending member 516 is not rotationally movable relative to the tubular enclosure 520. In other embodiments, the illustrated living hinge may be replaced or supplemented by one or more pinned hinges.

As illustrated in FIGS. 6A-6D, the endoscope 600 also includes a sheath 630 to which the camera 610 is coupled at a distal end of the sheath 630. The tubular enclosure 620 is sized to fit within the sheath 630. The tubular enclosure 620 shown is a cannula capable of longitudinally sliding relative to the sheath 630 and relative to the camera 610. The tubular enclosure 620 is open at both its proximal and distal ends and includes solid walls. However, in other embodiments proximal and distal ends may be partially closed or closable and the walls may not extend completely around the perimeter of the tubular enclosure at some or all longitudinal distances along the tubular enclosure. Some embodiments of a tubular enclosure may include a distal end that is rounded or chamfered to lessen stresses at points of contact with other components that are distal of the tubular enclosure when the endoscope is change between states. To the extent that reference is made to a central longitudinal axis 650 extending from a tubular enclosure that is curved along all or part of its length, the central longitudinal axis 650 may be considered to extend substantially normally from a distal end of the tubular enclosure.

The camera 610 depicted is not capable of longitudinally sliding relative to the sheath 630 but may be rotated relative to the sheath 630 and the tubular enclosure 620, as discussed in more detail below. The endoscope 600 may be introduced into tissue with a longitudinal axis of the camera 610 substantially parallel with the central longitudinal axis 650 of the tubular enclosure 620. In the embodiment shown, the rotational coupling between the sheath 630 and the camera 610 may be stiff enough to resist rotation during introduction into tissue, as illustrated by the position shown in FIG. 6A. In FIGS. 6B and 6C, the camera 610 is shown following longitudinal sliding of the tubular enclosure 620 relative to the sheath 630. The camera 610 shown includes a camera body 615 with the distal end 612 and a relatively short proximally extending member 616 that is coupled to the camera body 615. In some embodiments, one or both of the proximally extending member 616 and the camera body 615 may include along at least part of their lengths a lateral spring force configured to bias one or both of the proximally extending member 616 and the camera body 615 into a curved shape. For example, lateral spring forces may exist in the components that tend to push the distal end 612 toward the central longitudinal axis 650 of the tubular enclosure 620. Lateral spring forces of some embodiments may exist along the entire lengths of the proximally extending member 616 and the camera body 615 or may be limited to specific segments of either. As shown in FIGS. 6A-6C, the camera 610 may include a proximally directed surface 617 shaped so that when the proximally directed surface 617 is contacted by the tubular enclosure 620, the tubular enclosure 620 moves the camera 610 from the first coupled position toward the second coupled position. As shown in this example, the proximally directed surface 617 is a curved surface, and may have a radius of curvature as discussed above in reference to FIG. 3E. In some embodiments, a proximally directed surface may include compound curved surfaces that interact with a tubular enclosure to control rates and amounts of deflections of the camera 610 in response to movements of the tubular enclosure 620. In some embodiments, a proximally directed surface may have one or more planar surfaces with at least one surface being in a different plane from surfaces of the tubular enclosure 620 configured to contact the proximally directed surface.

A direct but movable coupling exists between the camera 610 and the sheath 630 about an axis 660 (FIGS. 6B and 6C) transverse to the central longitudinal axis 650 of the tubular enclosure 620 in the illustrated embodiment. The movable coupling between the camera 610 and the tubular enclosure 620 includes a mechanism for longitudinal sliding between the camera 610 and the tubular enclosure 620, as illustrated in the changes of relative state illustrated in FIGS. 6A-6C. In addition, in the illustrated embodiment, the movable coupling between the camera 610 and the tubular enclosure 620 includes a mechanism for movement substantially about the axis 660 (FIGS. 6B and 6C) transverse to the central longitudinal axis 650 of the tubular enclosure 620. The illustrated embodiment shows a living hinge between the camera 610 and the tubular enclosure 620 to the extent that the living hinge at the axis 660 is within a portion of the camera 610 between the camera body 615 and the proximally extending member 616, and the proximally extending member 616 is not rotationally movable relative to the tubular enclosure 620. In other embodiments, the illustrated living hinge may be replaced or supplemented by one or more pinned hinges.

Each of the illustrated endoscope embodiments 300, 400, 500, 600 includes the camera 310, 410, 510, 610 and the tubular enclosure 320, 420, 520, 620 through which a surgical act may be performed. The camera 310, 410, 510, 610 in a first position (FIGS. 3A, 4A, 5A, 6A, respectively) is coupled to the tubular enclosure 320, 420, 520, 620 such that the distal end 312, 412, 512, 612 of the camera 310, 410, 510, 610 is positioned on the central longitudinal axis 350, 450, 550, 650 of the tubular enclosure 320, 420, 520, 620. Each of the illustrated endoscope embodiments 300, 400, 500, 600 also includes means for moving the camera 310, 410, 510, 610 from the first position to a second position wherein the distal end 312, 412, 512, 612 of the camera 310, 410, 510, 610 is not positioned on the central longitudinal axis 350, 450, 550, 650 of the tubular enclosure 320, 420, 520, 620. In each of the illustrated embodiments, viewing from the camera 310, 410, 510, 610 is continuously unobstructed by the endoscope 300, 400, 500, 600 at the distal end 312, 412, 512, 612 of the camera 310, 410, 510, 610 when the camera 310, 410, 510, 610 is moved relative to the tubular enclosure 320, 420, 520, 620 from the first position to the second position.

A method embodiment is a method of positioning a camera at different perspectives. In the illustrated embodiments, the camera is a component of an endoscope. For illustrative purposes, and without limiting the scope of the method disclosed, the four endoscopes 300, 400, 500, 600 disclosed herein will be referenced in describing the method. The method may include coupling a camera 310, 410, 510, 610 having a distal end 312, 412, 512, 612 to a tubular enclosure 320, 420, 520, 620. The mechanisms for coupling are different for each of the endoscopes 300, 400, 500, 600, but operation of each mechanism is within the method disclosed. The endoscope 300 includes the camera 310 that is coupled with the tubular enclosure 320 by a proximally extending member 316 of the camera 310 being captured between the tubular enclosure 320 and the sheath 330 at each state of movement illustrated in FIGS. 3A-3C. As shown in FIGS. 1-3A, the distal end 312 of the camera 310 is positioned on the central longitudinal axis 350 of the tubular enclosure 320 in a first state. Movement of the camera 310 and the tubular enclosure 320 relative to one another, as illustrated in the state change between FIG. 3A and FIG. 3B, causes movement to a second position where the distal end 312 of the camera 310 is not positioned on the central longitudinal axis 350 of the tubular enclosure 320. Movement between the tubular enclosure 320 and the camera 310 in this embodiment also includes a distal end of the tubular enclosure 320 pushing against a proximally directed surface 317 of the camera 310 to flex the distal end 312 of the camera 310 away from the central longitudinal axis 350. In this embodiment, the moving act is carried out without at any time obstructing a view from the distal end 312 of the camera 310 by any portion of the endoscope 300. This unobstructed view may be useful when an intermediate perspective for positioning the distal end 312 of the camera 310 is needed. In other words, a user may want the perspective of either the state illustrated in FIG. 3B or FIG. 3C, or any intermediate perspective between the states of FIG. 3A and FIG. 3C, without a portion of the endoscope 300 blocking a view of the camera 310 when at or between any perspective.

The endoscope 400 includes the camera 410 that is coupled with the tubular enclosure 420 by placing the camera 410 within the tubular enclosure 420. As depicted in FIG. 4, the proximally extending member 416 of the camera 410 includes a lateral spring force. When placed in the tubular enclosure 420 and then moved from the distal end of the tubular enclosure 420, this lateral spring force urges the distal end 412 of the camera 410 from the position shown in FIG. 4A to the position shown in FIG. 4B. The distal end 412 of the camera 410 is positioned on the central longitudinal axis 450 of the tubular enclosure 420 in a first state in FIG. 4A. Movement of the camera 410 and the tubular enclosure 420 relative to one another, as illustrated in the state change between FIG. 4A and FIG. 4B, causes movement to a second position where the distal end 412 of the camera 410 is not positioned on the central longitudinal axis 450 of the tubular enclosure 420. As noted, lateral movement of the distal end 412 of the camera 410 in this embodiment is urged by a lateral spring force in the proximally extending member 416. In this embodiment, the moving act is carried out without at any time obstructing a view from the distal end 412 of the camera 410 by any portion of the endoscope 400. This unobstructed view may be useful when an intermediate perspective for positioning the distal end 412 of the camera 410 is needed. In other words, a user may want the perspective of either the state illustrated in FIG. 4B or FIG. 4C, or any intermediate perspective between the states of FIG. 4A and FIG. 4C, without a portion of the endoscope 300 blocking a view of the camera 310 when at or between any perspective.

The endoscope 500 includes the camera 510 that is coupled with the tubular enclosure 520 by coupling the camera 510 along an outer portion of the tubular enclosure 520. As most clearly illustrated in FIG. 5D, the illustrated embodiment includes a dovetail joint between the camera 510 and the tubular enclosure 520. The dovetail notch 524 extends substantially along the length of the proximally extending member 516 of the camera 510, but not into the camera body 515. The dovetail spline 522 on the tubular enclosure 520 cooperates with the dovetail notch 524 to provide for movement of the camera 510 and the tubular enclosure 520 relative to each other parallel with the central longitudinal axis 550 without allowing movement of the camera 510 laterally away from the tubular enclosure 520 where the tubular enclosure 520 and the camera 510 are coupled, which is along the dovetail notch 524 in this embodiment. As shown in FIG. 5A, the distal end 512 of the camera 510 is positioned on the central longitudinal axis 550 of the tubular enclosure 520 in a first state. Movement of the camera 510 and the tubular enclosure 520 relative to one another, as illustrated in the state change between FIG. 5A and FIG. 5B, causes movement to a second position where the distal end 512 of the camera 510 is not positioned on the central longitudinal axis 550 of the tubular enclosure 520. Movement between the tubular enclosure 520 and the camera 510 in this embodiment also includes a chamfered distal end 527 of the tubular enclosure 520 pushing against a proximally directed surface 517 of the camera 510 to flex the distal end 512 of the camera 510 away from the central longitudinal axis 550. In this embodiment, the moving act is carried out without at any time obstructing a view from the distal end 512 of the camera 510 by any portion of the endoscope 500. This unobstructed view may be useful when an intermediate perspective for positioning the distal end 512 of the camera 510 is needed. In other words, a user may want the perspective of either the state illustrated in FIG. 5B or FIG. 5C, or any intermediate perspective between the states of FIG. 5A and FIG. 5C, without a portion of the endoscope 500 blocking a view of the camera 510 when at or between any perspective.

The endoscope 600 includes the camera 610 that is coupled with the tubular enclosure 620 by a proximally extending member 616 of the camera 610 being coupled to the sheath 630 and the tubular enclosure 620 is captured within the sheath 630. As shown in FIG. 6A, the distal end 612 of the camera 610 is positioned on the central longitudinal axis 650 of the tubular enclosure 620 in a first state. Movement of the camera 610 and the tubular enclosure 620 relative to one another, as illustrated in the state change between FIG. 6A and FIG. 6B, causes movement to a second position where the distal end 612 of the camera 610 is not positioned on the central longitudinal axis 650 of the tubular enclosure 620. Movement between the tubular enclosure 620 and the camera 610 in this embodiment also includes a distal end of the tubular enclosure 620 pushing against a proximally directed surface 617 of the camera 610 to flex the distal end 612 of the camera 610 away from the central longitudinal axis 650. In this embodiment, the moving act is carried out without at any time obstructing a view from the distal end 612 of the camera 610 by any portion of the endoscope 600. This unobstructed view may be useful when an intermediate perspective for positioning the distal end 612 of the camera 610 is needed. In other words, a user may want the perspective of either the state illustrated in FIG. 6B or FIG. 6C, or any intermediate perspective between the states of FIG. 6A and FIG. 6C, without a portion of the endoscope 600 blocking a view of the camera 610 when at or between any perspective.

Various embodiments of an endoscope wholly or its components individually may be made from any biocompatible material. For example and without limitation, biocompatible materials may include in whole or in part: non-reinforced polymers, reinforced polymers, thermoplastics, metals, ceramics, adhesives, reinforced adhesives, and combinations of these materials. Reinforcing of polymers may be accomplished with carbon, metal, or glass or any other effective material. Examples of biocompatible polymer materials include polyamide base resins, polyethylene, Ultra High Molecular Weight (UHMW) polyethylene, low density polyethylene, polymethylmethacrylate (PMMA), polyetheretherketone (PEEK), polyetherketoneketone (PEKK), polymeric hydroxyethylmethacrylate (PHEMA), and polyurethane, any of which may be reinforced. Example biocompatible metals include stainless steel and other steel alloys, cobalt chrome alloys, zirconium, oxidized zirconium, tantalum, titanium, titanium alloys, titanium-nickel alloys such as Nitinol and other superelastic or shape-memory metal alloys.

Terms such as proximal, distal, lateral, near, far, away, small, and the like have been used relatively herein. However, such terms are not limited to specific coordinate orientations, distances, or sizes, but are used to describe relative positions or sizes referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. An endoscope comprising:
   a camera having a central longitudinal axis and a field of view within an angle between an upper boundary line and a lower boundary line; and
   a cannula having a central longitudinal axis and configured to couple to the camera to move the camera between a first position and a second position, wherein:
   in the first position, the central longitudinal axis of the camera is coaxial with the central longitudinal axis of the cannula, and the field of view of the camera is angled away from the central longitudinal axis of the cannula with the upper boundary line of the field of view parallel to the central longitudinal axis of the cannula; and
   in the second position, the central longitudinal axis of the camera is not coaxial with the central longitudinal axis of the cannula, and the field of view of the camera is angled toward the central longitudinal axis of the cannula with the lower boundary line of the field of view parallel to the central longitudinal axis of the cannula.

2. The endoscope of claim 1, wherein viewing from the camera is unobstructed by the endoscope at a distal end of the camera while the camera is moved.

3. The endoscope of claim 1, wherein a proximal portion of the camera includes a hinge.

4. The endoscope of claim 3, wherein the hinge defines an axis of rotation perpendicular to the central longitudinal axis of the cannula.

5. The endoscope of claim 3, wherein the hinge is a living hinge.

6. The endoscope of claim 1, wherein the camera includes a proximally directed surface shaped so that when the proximally directed surface is contacted by the cannula, the cannula moves the camera from the first position toward the second position.

7. The endoscope of claim 6, wherein the proximally directed surface is a curved surface that defines a radius of curvature being at least twice an outside diameter of the camera.

8. The endoscope of claim 6, wherein the proximally directed surface has a lateral spring force to bias the proximally directed surface into a curved shape.

9. The endoscope of claim 1, wherein the camera includes a camera body, the camera body including a lateral spring force configured to bias the camera toward the first position.

10. The endoscope of claim 1, wherein the camera includes a proximally extending member, the proximally extending member configured to impart a lateral spring force to bias the camera toward the first position.

11. The endoscope of claim 1, wherein the camera is slidingly coupled to the cannula by a coupling.

12. The endoscope of claim 11, wherein the coupling is a dovetail joint formed by a dovetail spline defined on one of the camera or the cannula and a dovetail notch defined on one of the camera or the cannula.

13. The endoscope of claim 1, wherein a distal end of the cannula includes a chamfered distal surface.

* * * * *